United States Patent [19]

Hartmann et al.

[11] Patent Number: 5,779,978
[45] Date of Patent: Jul. 14, 1998

[54] MEASURING ASSEMBLY FOR LUMINESCENCE ANALYSIS

[75] Inventors: Paul Hartmann, Weiz; Werner Ziegler, Graz; Hellfried Karpf, Graz; Johann Harer, Graz, all of Austria

[73] Assignee: AVL Medical Instruments AG, Schaffhausen, Switzerland

[21] Appl. No.: 797,249

[22] Filed: Feb. 7, 1997

[30] Foreign Application Priority Data

Feb. 29, 1996 [AT] Austria .................. 383/96

[51] Int. Cl.⁶ .................................... G01N 21/64
[52] U.S. Cl. .................... 422/82.05; 422/82.08; 422/82.11
[58] Field of Search .................. 422/82.05, 82.06, 422/82.07, 82.08, 82.11, 116; 436/172; 356/244, 246

[56] References Cited

U.S. PATENT DOCUMENTS

| | | | |
|---|---|---|---|
| 3,604,927 | 9/1971 | Hirschfeld | 356/244 |
| 4,399,099 | 8/1983 | Buckles | 422/82.11 |
| 4,810,658 | 3/1989 | Shanks et al. | 422/82.11 |
| 4,968,632 | 11/1990 | Brauer et al. | |
| 5,039,490 | 8/1991 | Marsoner et al. | |
| 5,260,029 | 11/1993 | Hosoi et al. | 422/82.08 |
| 5,370,842 | 12/1994 | Miyazaki et al. | 422/82.06 |
| 5,439,647 | 8/1995 | Saini | 422/82.11 |
| 5,623,561 | 4/1997 | Hartman | 385/12 |
| 5,672,515 | 9/1997 | Furlong | 436/172 |
| 5,694,215 | 12/1997 | Carver | 356/246 |

FOREIGN PATENT DOCUMENTS

| | | |
|---|---|---|
| 383684 | 8/1987 | Austria . |
| 0354895 | 9/1995 | European Pat. Off. . |
| 9427137 | 11/1994 | WIPO . |

*Primary Examiner*—Jeffrey Snay
*Attorney, Agent, or Firm*—Watson Cole Grindle Watson, P.L.L.C.

[57] ABSTRACT

A measuring assembly comprises a supporting element transparent to excitation and measurement radiation, which is provided with a number of preferably different luminescence-optical sensor elements on a first boundary face. Via a second boundary face excitation radiation can be picked up, and a third boundary face is used to supply measurement radiation of the sensor elements to a detector of an evaluation unit. The direction of the excitation radiation is essentially normal to that of detection. The preferably different sensor elements are connected by a common sample channel, and optical and/or temporal separation of the measurement radiation of the individual sensor elements is provided.

15 Claims, 3 Drawing Sheets

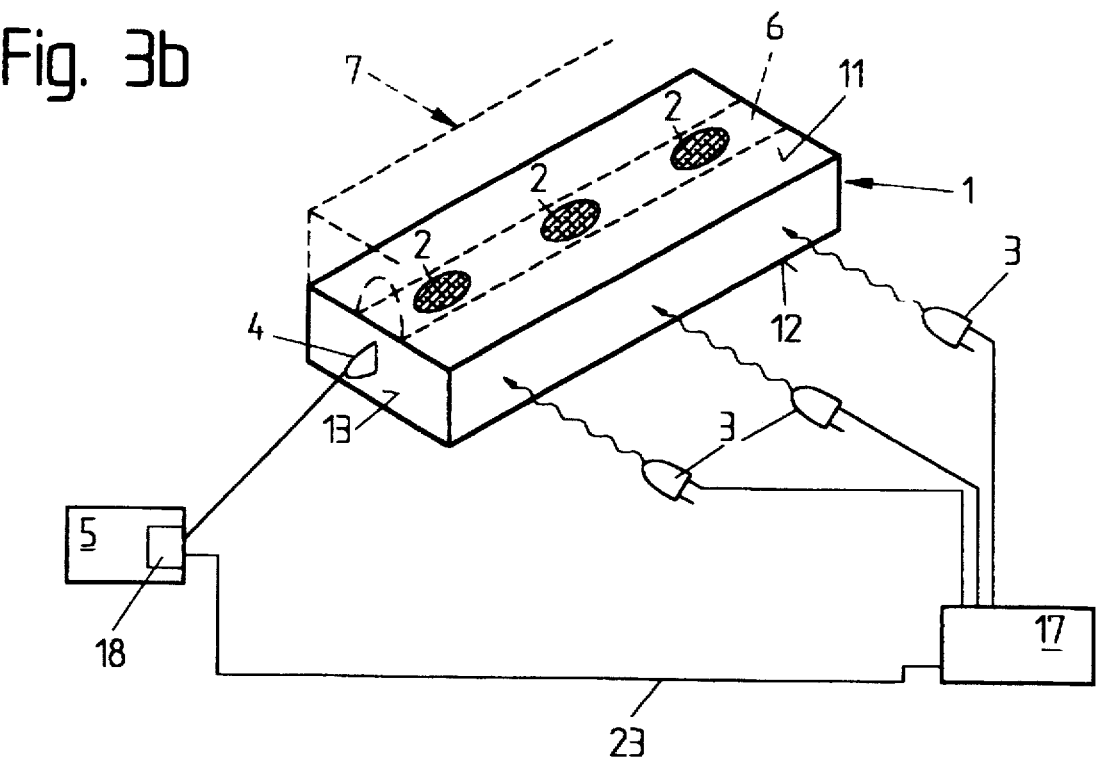
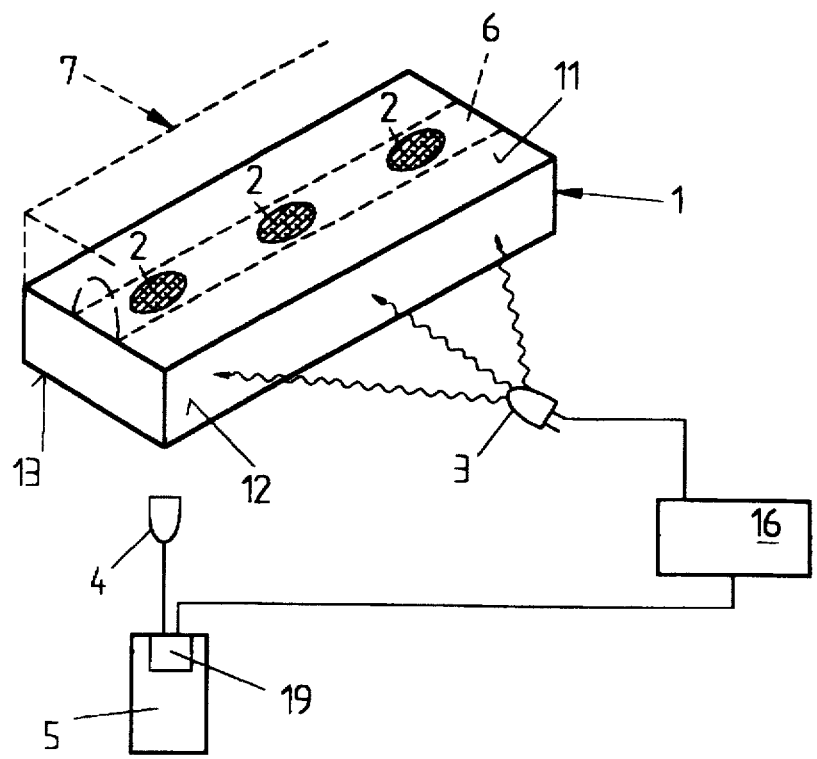

MEASURING ASSEMBLY FOR LUMINESCENCE ANALYSIS

BACKGROUND OF THE INVENTION

This invention relates to a measuring assembly comprising a supporting element transparent to excitation and measurement radiation, which is provided with a luminescence-optical sensor element on a first boundary face, and picks up excitation radiation from a radiation source via a second boundary face, and supplies measurement radiation of the sensor element to a detector of an evaluation unit via a third boundary face, the direction of the excitation radiation being essentially normal to that of detection, and the refractive index of the supporting element being greater than that of the environment.

DESCRIPTION OF THE PRIOR ART

A measuring assembly of the above type is described in AT-B 383 684. In that instance a transparent supporting element with plane-parallel boundary faces is furnished with a sensor layer on one of these faces, which is subject to excitation radiation from a radiation source. The light of the radiation source reaches the sensor layer through an aperture, and the resulting measurement radiation is transmitted to a detector in a direction essentially normal to that of the excitation radiation, the detector being positioned on a lateral boundary face of the supporting element. Light guidance inside the supporting element is effected essentially by total reflection of the measurement radiation at the boundary faces of the supporting element. On the boundary face carrying the sensor layer a sample chamber is provided, which has an inlet and an outlet for the sample to be passed through for analysis. The sample, or rather, the sample analyte to be measured, changes an optical property of the luminescence indicator in the sensor layer, resulting in a change of the measurement radiation detected by the detector in functional dependence of the analyte concentration.

EP-B1 0 354 895 presents a oneway measuring element for simultaneous analysis of a number of different sample components, comprising a sensing unit and a sampling unit connected thereto. The sensing unit features a sample channel containing several sensors. Excitation of the sensors and detection of the measurement radiation are effected by means of light guides to each individual sensor, the light signals being evaluated in an excitation and measuring unit which is not shown in detail.

In U.S. Pat. No. 4,968,632 a method and device for quick sample analysis are disclosed. A sample chamber with transparent opposing walls is provided on the inside with a luminescence indicator which is contained in a indicator layer. The excitation radiation emitted by several light sources reaches the sample—e.g., a gas interacting with the indicator layer—through a transparent wall of the measuring chamber. A number of filters are provided in the area of the indicator layer, each filtering out a certain component of the measurement radiation, and each filter being provided with a photodiode for detection of the measurement radiation. The quantity to be measured is determined from characteristic changes in the individual spectra. A sensor element for simultaneous determination of the concentrations of several substances in a sample is also described in U.S. Pat. No. 5,039,490. A multilayer sensor element is provided with photosensitive elements and light-emitting sources placed side by side, which are covered by a transparent coupling layer. The coupling layer is covered by an indicator layer, which in turn may be covered by a cover layer in contact with the sample. The somewhat complicated sensor element requires filters or optical gratings to avoid backscattering of the excitation light into the photosensitive elements. By using different indicator substances for the individual photosensitive elements several different sample components may be determined simultaneously.

SUMMARY OF THE INVENTION

It is an object of the present invention to propose a measuring assembly on the basis of the above state of the art devices, which is simple and inexpensive to produce and permits simultaneous measurement of several different sample components without necessitating the use of filters and optical gratings in the supporting element. A further requirement is to design the supporting element of the assembly as a oneway element.

In the invention this object is achieved by positioning several preferably different sensor elements on the first boundary face, which are connected by a common sample channel, and by providing means for optical and/or temporal separation of the light paths of the measurement radiation of the individual sensor elements.

It is an advantage in this context to effect separation not only of the excitation radiation from the measurement radiation by different optical paths, but also of the measurement radiations emitted by the individual sensor elements by optically and/or temporally separating the light paths, as will be described in greater detail below. As a consequence, no optical filters or grating structures will be required in the supporting element.

In a first variant of the invention it is proposed that for the purpose of optically separating the light paths of the measurement radiations emitted by the individual sensor elements, the supporting element exhibit, along the sample channel and normal thereto, constrictions, recesses and/or layers or regions that are impervious to the measurement radiation, each sensor element being assigned a detector of the evaluation unit. The supporting element may essentially feature a comb structure carrying the individual sensor elements along its base, the comb structure showing an essentially prism-shaped projection in the area of each sensor element, whose front face is furnished with a detector.

Another variant of the invention provides that the supporting element have one or more optoelectronic switching elements in the light path of the measurement radiation of each sensor element, which switching elements will open only one light path at a time between a sensor element and the detector of the evaluation unit.

According to a particularly advantageous embodiment of the invention each sensor element is provided with a separate radiation source, and all sensor elements are assigned one common detector.

The separate radiation sources may be connected to an electronic control unit permitting the emission of excitation radiation sequenced in time (multiplexing), such that the separation of the light paths of the measurement radiation of each sensor element is achieved by time-shifted excitation of the sensor elements.

It could also be provided, however, that the separate radiation sources be connected to another electronic device for periodic modulation of the excitation radiation, and that the detector be connected with a device for periodically modulated detection of the measurement radiation, where the light paths of the measurement radiation of each sensor element are separated by measuring the phase angle and/or the demodulation between excitation and measurement radiation. The decay time or its change thus may also be obtained from the demodulation, i.e., reduction of the amplitude of the measurement radiation vis-a-vis the excitation radiation.

In yet another variant of the invention the proposal is put forward that all sensor elements be in optical connection with a common, pulsed radiation source and a common detector, the detector being connected to a device for time-sequenced detection of the measurement radiation in order to separate the light paths of the measurement radiation of each sensor element. Separation of the light paths could also be effected by an additional unit for mathematical splitting of the decay time functions of the individual sensor elements. In this simple variant one radiation source and one common detector may be used for several sensor elements.

Pulsed excitation and subsequent decay time measurement are also useful in instances where a separate radiation source is assigned to each sensor element.

In variants in which all sensor elements are optically connected with a common detector, the decay time profiles of all sensor elements may be detected simultaneously, in which case the evaluation unit includes a subunit for mathematical splitting of the decay time functions of the individual sensor elements. With this variant the number of sensor elements is limited, however, depending on the extent to which the mean time constants of the decay times of the individual sensor elements differ from each other. Good measured results are obtained if the mean time constants of the decay times differ at least by a factor two.

According to the invention the supporting element may be suited for light guidance between the sensor elements and the detector or detectors by means of total reflection. Other variants are conceivable, however, in which the excitation radiation could also be guided between the light source and the sensor elements by means of total reflection in the supporting element.

In all variants the supporting element including sensor elements and sample channel may conveniently be configured as a cost-effective oneway element whose boundary faces are used as contact surfaces for the radiation sources and detectors located in a measuring assembly once the element has been inserted.

BRIEF DESCRIPTION OF THE DRAWINGS

The invention will now be further described with reference to the accompanying drawings, in which FIGS. 3a to 3c show measuring assemblies of the invention with identical supporting elements and different excitation and detection devices.

DETAILED DESCRIPTION OF PREFERRED EMBODIMENTS

Figure 1:
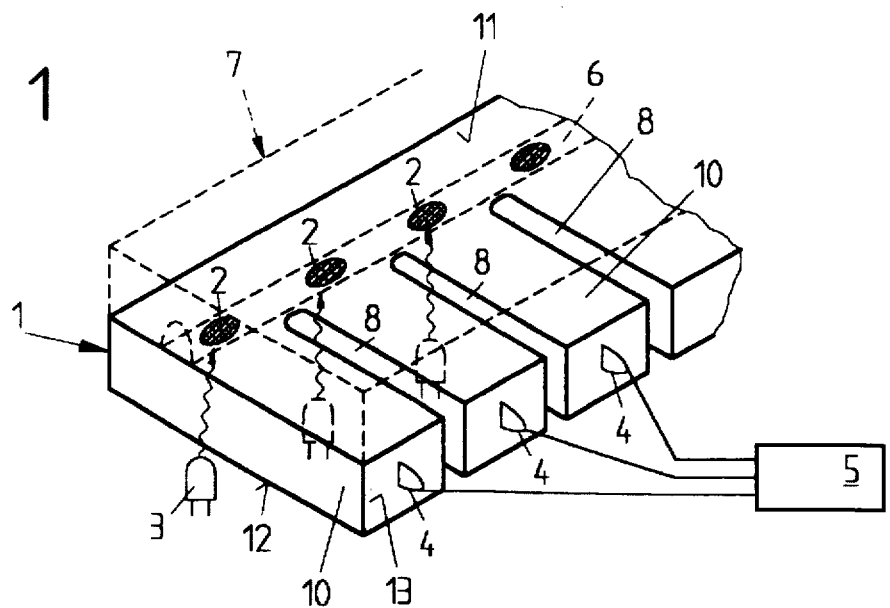
FIGS. 1 and 2 are schematical representations of measuring assemblies of the invention with separate detectors for each sensor element.

All variants of the measuring assembly described by the invention, which are presented in FIGS. 1 to 6, exhibit a supporting element 1 that is transparent to the excitation and measurement radiation used, where the luminescence-optical sensor elements 2, 2' are located on a boundary face 11, and excitation radiation is radiated in through a boundary face 12, and measurement radiation is given off via a boundary face 13. The light source(s) 3 are accordingly assigned to boundary face 12, and the detector(s) 4, 4' to boundary face 13. The signals of detectors 4, 4' are fed to an evaluation unit 5. The direction of the excitation radiation is essentially normal to the direction of detection, although angles of 60 to 120 degrees are permissible. All sensor elements 2, which are preferably provided with different indicator materials for measuring different parameters, are connected by a common sample channel 6. The capillary sample channel 6 and its housing structure 7 are only indicated schematically. The sample channel may have a square, rectangular or essentially semicircular cross-section, and could feature enlarged passages in the area of the individual sensor elements 2, 2'.

To effect an optical separation of the light paths of the measurement radiation emitted by the individual sensor elements 2 constrictions or recesses 8 are provided in the supporting element 1 according to the variant of FIG. 1, the refractive index n1 of element 1 being greater than that of its environment. The individual sensor elements 2 are simultaneously excited in this variant by radiation sources 3, such as LEDs. It would also be possible to use only one radiation source (FIG. 2), provided that a single source will suffice to excite the different indicator materials in sensor elements 2. The supporting element of FIG. 1 has a comb structure at whose lateral base are located the individual sensor elements which are connected by the common sample channel 6. The front faces of the finger-like, prismatic projections 10 each are assigned to a detector 4.

Figure 2:
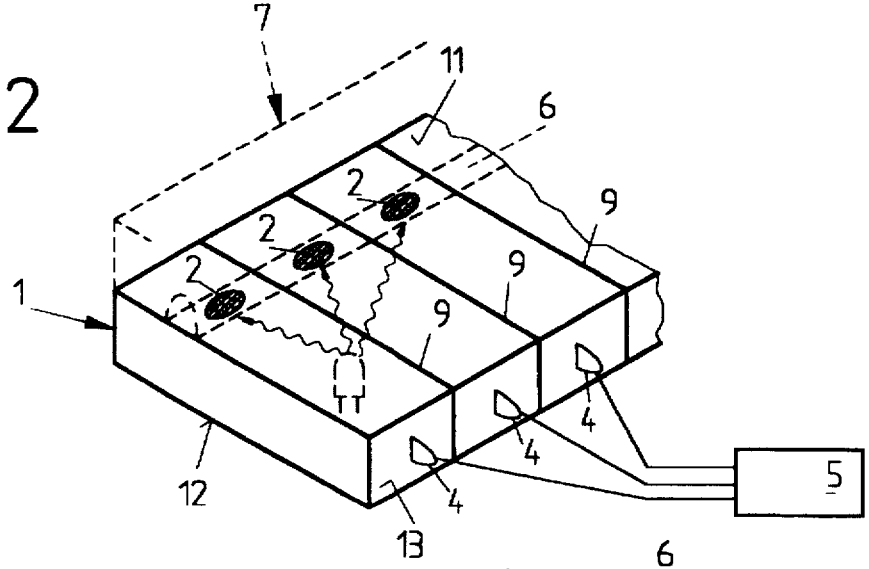

The variant of FIG. 2 differs from that of FIG. 1 in that the individual areas of supporting element 1, each of which carries a sensor element 2, are divided by layers 9 or reflective coatings that are impervious to the measurement radiation. In this way the measurement radiation is prevented from reaching detectors 4 not assigned to it.

Figure 3A:
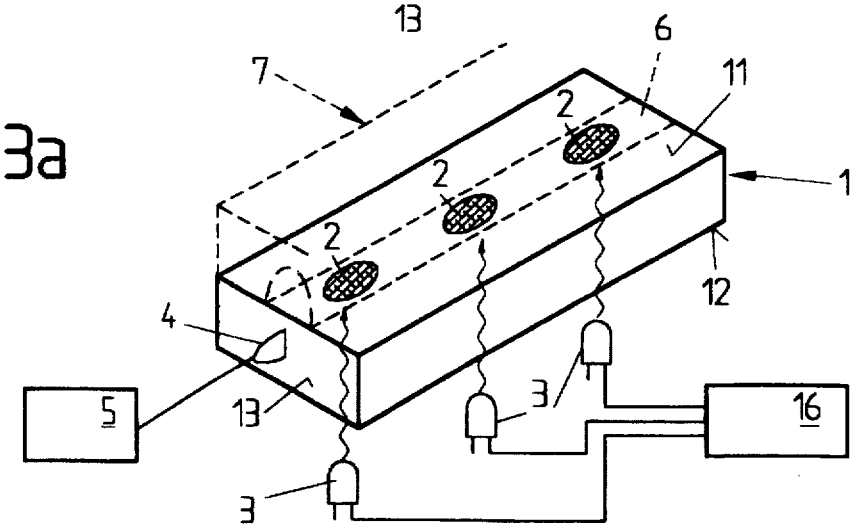

The variants of FIGS. 3a to 3c feature a supporting element 1 of very simple shape and design, for instance, a rectangular parallelepiped. On one of the oblong boundary faces 11 the individual sensor elements 2 are arranged, while boundary faces 12 and 13 are employed for transmitting the excitation radiation and detecting the measurement radiation, respectively. A second similar component or housing 7, into which the sample channel 6 is cut as a groove, for example, may be glued to the supporting element 1, or bonded thereto by other suitable means.

The variant of FIG. 3a has separate radiation sources 3 for each sensor element 2, and a detector 4 on the front face. In this instance excitation takes place in time-sequenced fashion via a device 16, using the so-called multiplexing method. Simultaneous measurement in this context means determination of several parameters while the sample is introduced into the sample channel only once.

In FIG. 3b the individual radiation sources are assigned to a lateral face 12 of the supporting element, and excitation of the individual sensor elements is effected either by the evanescent portion of the excitation wave, or by suitably adapting the refractive index in the region of the sensor spots. In this variant the excitation radiation is periodically modulated via a device 17, device 18 providing a periodically modulated detection of the measurement radiation. Devices 17 and 18 are connected to a signal lead 23, which will permit the phase angle and/or demodulation between excitation and measurement radiation to be measured in the evaluation unit.

FIG. 3c, finally, shows a variant of the invention in which one common, pulsed radiation source 3 and one common detector 4 are assigned to all sensor elements 2. After common, pulsed excitation of all sensor elements 2, detection takes place using measuring points or windows shifted in time. In this variant there should be significant differences in the mean time constants of the decay times of the individual sensor elements. The detector 4 may be followed by a unit 19 for mathematical splitting of the decay time functions of the individual sensor elements.

Figure 4:
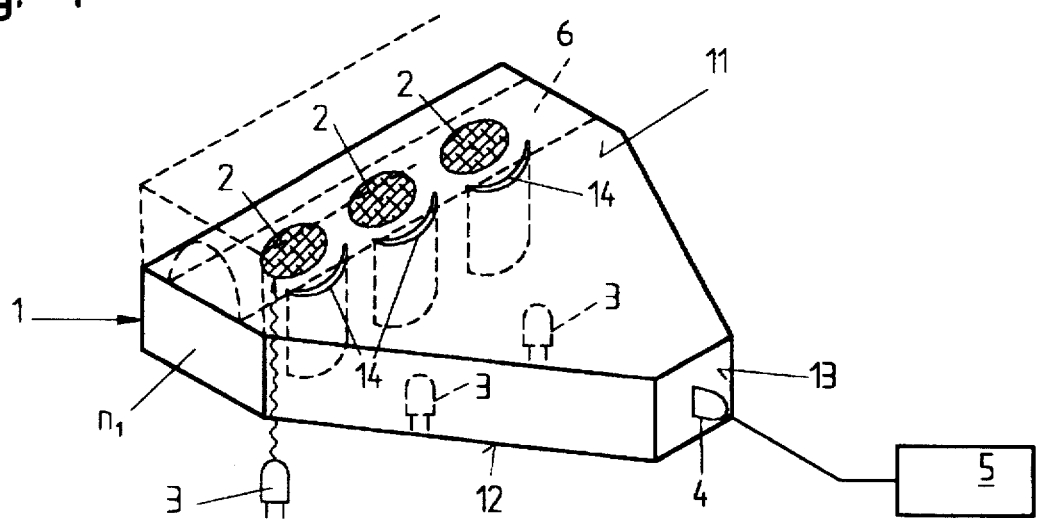
FIGS. 4 to 6 show other advantageous variants of the invention.

In the variant of FIG. 4 the supporting element 1 is provided with an optoelectronic switching element 14 in the light path of the measurement radiation of each sensor element 2. With the use of this switching element one defined light path at a time is opened between one of the sensor elements 2 and the detector 4.

Figure 5:
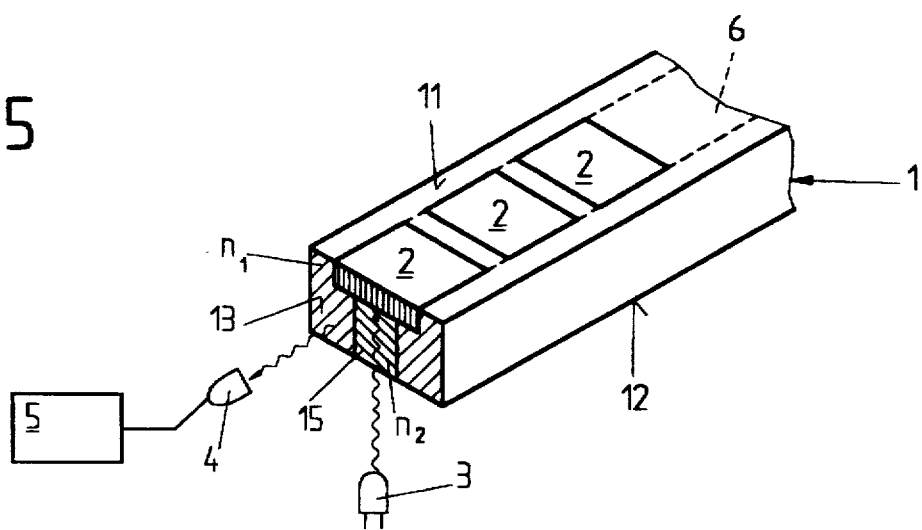

A variant of the embodiments according to FIGS. 3a to 3c is shown in FIG. 5. The supporting element 1 features delimited regions 15 in the area of the sensor elements 2, whose refractive index $n_2$ is greater than the refractive index $n_1$ of the supporting element itself. Via the regions 15 with the larger refractive index $n_2$ excitation radiation may be supplied directly and/or by total reflection. The fluorescence radiation emitted in all directions in space will reach among others the lateral areas of the supporting element 1, from where it is transmitted, directly and/or by means of total reflection, to one of the two front faces 13, and detected by detector 4.

Figure 6:
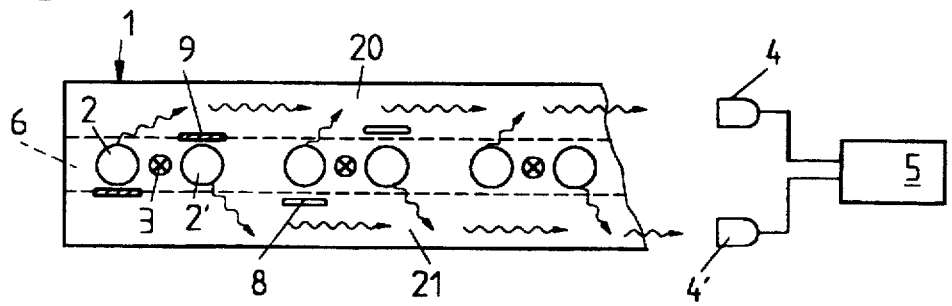

A very compact variant of the invention is presented in FIG. 6. In this instance every two sensor elements 2, 2' are combined into pairs, each pair being assigned a separate radiation source 3. In a compact design as many as eight different sensor elements can be excited by up to four light emitting diodes in this way. Each first sensor element 2 of a pair is assigned a first detector 4 via a first light path 20, and each second sensor element 2' is assigned a second detector 4' via a second light path 21 in the supporting element 1. Recesses 8 or opaque layers that are impervious to light may be used to block the alternative light path. Separation of the light paths of different pairs of sensor elements 2, 2' may be effected by time-sequenced excitation of the individual pairs, or modulated excitation and detection.

We claim:

1. A measuring assembly comprising at least one radiation source, at least one detector and a supporting element being transparent to excitation and measurement radiation and having first, second and third boundary faces, said supporting element being provided with several luminescence-optical sensor elements on said first boundary face, and picks up excitation radiation from said radiation source via said second boundary face, and supplies measurement radiation of said sensor elements to said detector of an evaluation unit via said third boundary face, the direction of said excitation radiation being essentially normal to the direction of detection, and the refractive index $n_1$ of said supporting element being greater than the refractive index of the environment, wherein said several sensor elements are connected by a common sample channel, and wherein means are provided for optical or temporal separation of light paths of said measurement radiation emitted by said individual sensor elements.

2. A measuring assembly according to claim 1, wherein said supporting element exhibits, along said sample channel and normal thereto, constrictions, recesses, layers or regions being impervious to said measurement radiation, for the purpose of optically separating said light paths of said measurement radiation emitted by said individual sensor elements and wherein each of said sensor elements is assigned a detector of said evaluation unit.

3. A measuring assembly according to claim 2, wherein said supporting element essentially features a comb structure carrying said individual sensor elements along its base said comb structure showing essentially prism-shaped projections in the area of each of said sensor elements, wherein the front faces of said projections are furnished with said detectors.

4. A measuring assembly according to claim 1, wherein said supporting element comprises optoelectronic switching elements situated in said light path of said measurement radiation of each of said sensor elements for opening only one light path at a time between one of said sensor elements and said at least one detector of said evaluation unit.

5. A measuring assembly according to claim 1, wherein each of said sensor elements is provided with a separate radiation source, and all of said sensor elements are assigned one common detector of said evaluation unit.

6. A measuring assembly according to claim 5, wherein said separate radiation sources are connected to an electronic control unit permitting the emission of excitation radiation sequenced in time, such that separation of said light paths of said measurement radiation of each of said sensor elements is achieved by time-shifted excitation of said sensor elements.

7. A measuring assembly according to claim 5, wherein said separate radiation sources are connected to an electronic device for periodic modulation of said excitation radiation, and wherein said detector is connected with a device for periodically modulated detection of said measurement radiation, the light paths of said measurement radiation of each of said sensor elements being separated by measuring the phase angle or the demodulation between said excitation radiation and said measurement radiation.

8. A measuring assembly according to claim 5, wherein said separate radiation sources are furnished with a device for pulsed excitation of said sensor elements, and wherein said detector is connected with a device for time-sequenced detection of said measurement radiation.

9. A measuring assembly according to claim 5, wherein said supporting element features delimited regions in the area of each of said sensor elements, said delimited regions having a refractive index $n_2$ being greater than the refractive index $n_1$ of said supporting element outside of said delimited regions, wherein said excitation radiation is fed in in said delimited regions with refractive index $n_2$ and said measurement radiation is carried off in the remaining regions of said supporting element having a refractive index $n_1$.

10. A measuring assembly according to claim 1, wherein all of said sensor elements are in optical connection with a common, pulsed radiation source and a common detector, said detector being connected to a device for time-sequenced detection of said measurement radiation in order to separate the light paths of said measurement radiation of each of said sensor elements.

11. A measuring assembly according to claim 1, wherein all of said sensor elements are in optical connection with a common detector, which is provided with a device for simultaneous detection of decay time profiles of all of said sensor elements, and wherein said evaluation unit includes a subunit for mathematical splitting of the decay time functions of said individual sensor elements.

12. A measuring assembly according to claim 1, wherein said sensor elements are combined into pairs, each of said pairs being assigned a separate radiation source, and wherein said evaluation unit is connected to first and second detectors, each first sensor element of a pair of sensor elements being assigned said first detector via a first light path in said supporting element, and each second sensor element of a pair of sensor elements being assigned said second detector via a second light path in said supporting element, and wherein the separation of said light paths of different pairs of sensor elements being effected by time-sequenced excitation of said individual pairs.

13. A measuring assembly according to claim 1, wherein said supporting element is suited for light guidance between said sensor elements and said at least one detector by means of total reflection.

14. A measuring assembly according to claim 1, wherein said supporting element including said sensor elements and said sample channel is configured as a oneway element and said second and third boundary faces are used as contact surfaces for said radiation sources and said at least one detector located in a measuring assembly.

15. A measuring assembly according to claim 1, wherein said sensor elements are responsive to different analytes.

* * * * *